(12) United States Patent
Kinsley et al.

(10) Patent No.: US 9,404,813 B2
(45) Date of Patent: Aug. 2, 2016

(54) SYSTEMS AND METHODS FOR DETERMINING PATIENT TEMPERATURE

(71) Applicant: Welch Allyn, Inc., Skaneateles Falls, NY (US)

(72) Inventors: Matthew J. Kinsley, Marcellus, NY (US); David E. Quinn, Auburn, NY (US); John A. Lane, Weedsport, NY (US); Michael J. Anson, Canton, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 0 days.

(21) Appl. No.: 14/668,647

(22) Filed: Mar. 25, 2015

(65) Prior Publication Data
US 2015/0198489 A1 Jul. 16, 2015

Related U.S. Application Data

(63) Continuation of application No. 13/186,072, filed on Jul. 19, 2011, now Pat. No. 8,996,096.

(51) Int. Cl.
| A61B 6/00 | (2006.01) |
| G01J 5/00 | (2006.01) |
| G01K 13/00 | (2006.01) |
| A61B 5/01 | (2006.01) |
| G01J 5/02 | (2006.01) |
| G01J 5/16 | (2006.01) |
| G01K 1/20 | (2006.01) |

(Continued)

(52) U.S. Cl.
CPC ............... *G01K 13/004* (2013.01); *A61B 5/01* (2013.01); *A61B 5/742* (2013.01); *G01J 5/0025* (2013.01); *G01J 5/021* (2013.01); *G01J 5/025* (2013.01); *G01J 5/16* (2013.01); *G01K 1/083* (2013.01); *G01K 1/20* (2013.01); *G01K 13/002* (2013.01); *A61B 5/0059* (2013.01); *A61B 5/6847* (2013.01); *A61B 2560/0223* (2013.01); *A61B 2562/12* (2013.01); *Y10T 29/49007* (2015.01); *Y10T 29/49117* (2015.01)

(58) Field of Classification Search
CPC ....... G01K 13/004; G01K 1/083; A61B 5/01; A61B 5/742; A61B 2562/12
See application file for complete search history.

(56) References Cited

U.S. PATENT DOCUMENTS

| 4,166,389 A | 9/1979 | Montren |
| 4,497,324 A | 2/1985 | Sullivan et al. |

(Continued)

FOREIGN PATENT DOCUMENTS

| JP | 2008-237397 A | 9/2008 |
| JP | 2009-119237 A | 4/2009 |
| WO | WO2010-078219 | 7/2010 |

OTHER PUBLICATIONS

International Search Report and Written Opinion for International Application No. PCT/US2012/031129, Mailed Oct. 12, 2012, (9 pages).

*Primary Examiner* — Lisa Caputo
*Assistant Examiner* — Janice M Soto

(57) ABSTRACT

A temperature probe includes a shaft having a distal end, a proximal end, and a tip disposed at the distal end. The probe also includes an infrared sensor configured to measure a temperature of a structure disposed proximate the shaft. The probe further includes a temperature sensor disposed distal to the infrared sensor. The temperature sensor is configured to measure a body cavity temperature of a patient.

26 Claims, 2 Drawing Sheets

(51) Int. Cl.
*G01K 1/08* (2006.01)
*A61B 5/00* (2006.01)

(56) References Cited

U.S. PATENT DOCUMENTS

| | | | |
|---|---|---|---|
| 4,784,149 A * | 11/1988 | Berman | A61B 5/0059 |
| | | | 374/129 |
| 4,787,149 A | 11/1988 | Possati et al. | |
| 5,232,284 A | 8/1993 | Egawa et al. | |
| 5,393,351 A * | 2/1995 | Kinard | H01L 35/08 |
| | | | 136/200 |
| 5,826,980 A | 10/1998 | Kouzu et al. | |
| D480,977 S | 10/2003 | Wawro et al. | |
| D481,321 S | 10/2003 | Knieriem et al. | |
| 6,839,651 B2 * | 1/2005 | Lantz | G01K 7/42 |
| | | | 374/128 |
| 7,434,992 B2 | 10/2008 | Tabata et al. | |
| 7,507,019 B2 | 3/2009 | Price | |
| 7,572,056 B2 | 8/2009 | Lane et al. | |
| 2006/0153278 A1 * | 7/2006 | Chen | G01J 5/02 |
| | | | 374/208 |
| 2007/0248141 A1 * | 10/2007 | Price | G01J 5/0022 |
| | | | 374/131 |
| 2008/0089387 A1 | 4/2008 | Price | |
| 2009/0285260 A1 | 11/2009 | Stone et al. | |
| 2010/0017163 A1 | 1/2010 | Yamaguchi et al. | |
| 2010/0091813 A1 | 4/2010 | Bellifemine | |
| 2010/0265986 A1 * | 10/2010 | Mullin | G01J 5/0003 |
| | | | 374/1 |
| 2011/0158283 A1 | 6/2011 | Meyerson et al. | |
| 2011/0257521 A1 | 10/2011 | Fraden | |

* cited by examiner

SYSTEMS AND METHODS FOR DETERMINING PATIENT TEMPERATURE

CROSS-REFERENCE TO RELATED APPLICATIONS

This Application is a continuation of U.S. application Ser. No. 13/186,072, filed Jul. 19, 2011, the entire disclosure of which is incorporated herein by reference.

FIELD OF THE INVENTION

The present disclosure relates to systems and methods for temperature determination and, in particular, to systems and methods of determining a predicted patient temperature.

BACKGROUND OF THE INVENTION

Measuring patient temperature is a common first step in diagnosing illnesses. Physicians commonly use a variety of methods for determining patient temperature including, for example, obtaining temperature measurements with a thermometer. While thermometers utilizing mercury have been in existence for many years, modern thermometers typically employ one or more electronic sensors configured to measure patient temperature. Such sensors may take one or more measurements over a relatively short period of time. Based on these measurements, the thermometer may generate a predicted internal and/or core temperature of the patient. In generating this predicted temperature, the thermometer may make one or more assumptions regarding the temperature of the environment in which the thermometer is being utilized. For example, it is common practice to insert at least a portion of the thermometer into a cover prior to taking temperature measurements. Known thermometers may then sense the ambient temperature, and use this sensed ambient temperature in determining a patient's core temperature.

Determining a patient's core temperature in this way may produce inaccurate results. For example, the covers utilized with such thermometers are often stored in locations having an ambient temperature different than the ambient temperature of the examination room, doctor's office, and/or other patient temperature measurement locations. As a result, variations in the temperature of the cover itself may cause significant error in the patient temperature determination. In an effort to minimize the effect of such error, modern thermometers may utilize algorithms that estimate this divergence from ambient temperature. Such estimates, however, may introduce additional error into the patient temperature determination, thereby reducing the accuracy of such determinations.

The exemplary embodiments of the present disclosure are directed toward overcoming the deficiencies of known thermometers described above.

SUMMARY

In an exemplary embodiment of the present disclosure, a temperature probe includes a shaft having a distal end, a proximal end, and a tip disposed at the distal end. The probe also includes an infrared sensor configured to measure a temperature of a structure disposed proximate the shaft. The probe further includes a temperature sensor disposed distal to the infrared sensor. The temperature sensor is configured to measure a body cavity temperature of a patient.

In an exemplary embodiment of the present disclosure, a method of determining a predicted patient temperature includes inserting a temperature probe into a probe cover, sensing a first temperature with the probe indicative of a probe cover temperature, and inserting the probe and the probe cover into a body cavity of a patient. The method also includes sensing a second temperature with the probe indicative of a body cavity temperature, and calculating the predicted patient temperature based on the first and second sensed temperatures.

In another exemplary embodiment of the present disclosure, a method of determining a predicted patient temperature includes inserting a temperature probe into a probe cover disposed within a storage container, sensing a first temperature with the probe indicative of a storage container temperature, and inserting the probe and the probe cover into a body cavity of a patient. The method also includes sensing a second temperature with the probe indicative of a body cavity temperature, and calculating the predicted patient temperature based on the first and second sensed temperatures.

DETAILED DESCRIPTION

Figure 1:
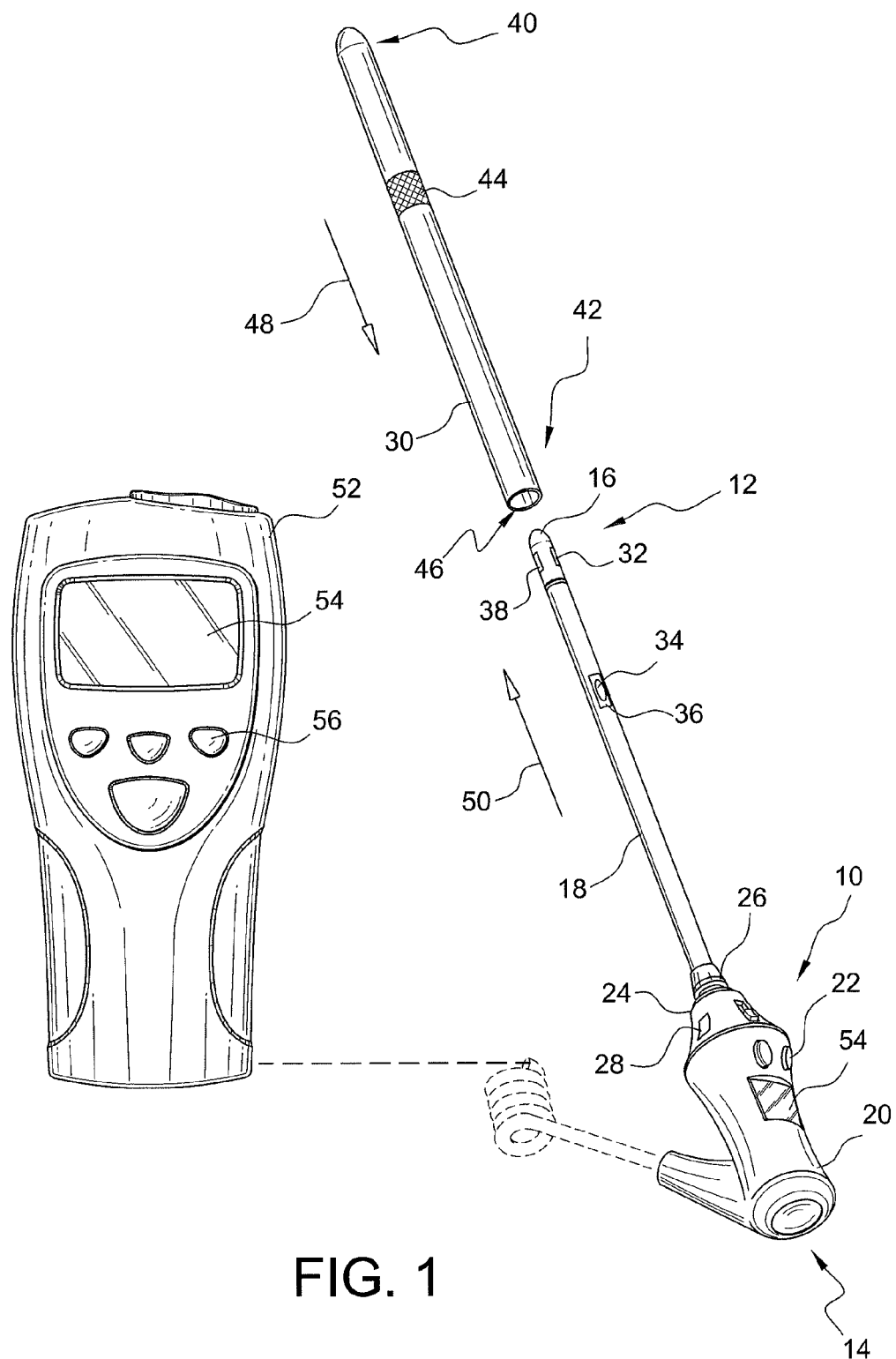
FIG. 1 illustrates a temperature probe according to an exemplary embodiment of the present disclosure.

FIG. 1 illustrates an exemplary temperature probe 10 of the present disclosure. The temperature probe 10 may include, for example, a shaft 18 connected to a handle 20. The shaft 18 may define a distal end 12 of the temperature probe 10, and the handle 20 may define a proximal end 14 of the probe 10. The shaft 18 may also define an atraumatic tip 16 disposed at the distal end 12. The tip 16 may be sufficiently rounded and/or otherwise configured so as not to cause injury to a patient upon at least partial insertion of the shaft 18 within one or more body cavities of the patient. In an exemplary embodiment in which the temperature probe 10 is utilized to measure, calculate, and/or otherwise determine a temperature of the patient, it is understood that such body cavities may include the mouth, rectum, underarm, and/or other known body cavities from which it is convenient to sense temperature. The shaft 18 and/or the handle 20 may be made from any material and/or combinations of materials commonly used in medical and/or examination procedures. Such materials may include, for example, plastics, polymers, composites, stainless steel, and/or any other like materials. Such materials may be suitable for repeated use and/or repeated sanitation. Accordingly, in an exemplary embodiment of the present disclosure, the temperature probe 10 and/or its components may be substantially waterproof. One or more waterproof seals may be included and/or otherwise utilized with components of the probe 10 to facilitate such repeated sanitation and/or use.

The handle 20 may include one or more operator interfaces 22. Such operator interfaces 22 may be configured to assist in performing one or more functions of the temperature probe 10. For example, the operator interfaces 22 may comprise any combination of switches, buttons, levers, knobs, dials, keys, and/or other like components configured to activate, deactivate, manipulate, and/or otherwise control components of the temperature probe 10. Such operator interfaces 22 may, for example, assist the user in toggling through and/or selecting one or more modes of operation of the temperature probe 10, enabling and/or disabling one or more alarms or signals associated with operation of the probe 10, initiating a single substantially instantaneous temperature calculation, initiating a substantially continuous and/or repeating temperature calculation, and/or other like modes, functions, or operations.

In an exemplary embodiment, at least one of the operator interfaces 22 may be operatively connected to an ejector mechanism 26 disposed proximate a base 24 of the shaft 18. As will be described in greater detail below, at least a portion of the temperature probe 10 may be inserted into a probe cover 30 before and/or during use, and such an ejector mechanism 26 may be configured to assist in removing the probe cover 30 from the temperature probe 10. For example, the ejector mechanism 26 may comprise one or more fingers, hooks, shoulders, arms, tabs, and/or other like structures configured to assist in ejecting the probe cover 30 from the base 24 of the shaft 18 after use. In an exemplary embodiment, one or more such ejector mechanisms 26 may be movable with respect to the base 24 and/or the shaft 18. In such exemplary embodiments, the ejector mechanisms 26 may be movable in, for example, a direction substantially parallel to the shaft 18. In additional exemplary embodiments, the ejector mechanisms 26 may be movable in an arcuate path relative to the shaft 18. Movement of the ejector mechanisms 26 may assist in bending, flexing, and/or otherwise deforming at least a portion of the probe cover 30. For example, the ejector mechanisms 26 may be movable along one or more surfaces of the probe cover 30, and such movement may assist in flexing at least a portion of the probe cover 30. Such flexing may ultimately overcome a retention force provided by one or more retention components (not shown) of the temperature probe 10, thereby releasing the probe cover 30 from the temperature probe 10.

In additional exemplary embodiments, one or more operator interfaces 22 may be configured to assist in controlling one or more corresponding sensors associated with the temperature probe 10. For example, the operator interfaces 22 may be operatively connected to first and second sensors 32, 34 disposed on the shaft 18. In exemplary embodiments, the first and second sensors 32, 34 may be embedded within and/or otherwise formed integrally with the shaft 18. In such exemplary embodiments, the sensors 32, 34 may be positioned just beneath an outer surface of the shaft 18 such that the shaft 18 may retain a substantially smooth, substantially cylindrical shape. In such exemplary embodiments, it is understood that the sensors 32, 34 may be electrically, operably, and/or otherwise connected to the operator interfaces 22 and/or other components of the temperature probe 10 via electrical connections embedded within and/or running along a length of the shaft 18 beneath the outer surface of the shaft 18.

In an exemplary embodiment, one or more of the sensors 32, 34 may comprise any type of temperature sensor known in the art. For example, the sensors 32, 34 may be the same type of sensor. The sensors 32, 34 may comprise different types of sensors configured to sense one or more different characteristics of a patient. In an exemplary embodiment, at least one of the first and second sensors 32, 34 may comprise a thermocouple and/or a thermistor configured to sense a temperature associated with such a patient. For example, such a sensor may be configured to sense a temperature of the body cavity into which the temperature probe 10 has been inserted. For example, in embodiments in which the shaft 18 of the temperature probe 10 is inserted into the mouth of the patient, such a sensor may be utilized to sense a temperature of the mouth.

At least one of the sensors 32, 34 may also comprise an infrared temperature sensor such as, for example, a thermopile and/or other like infrared-based temperature sensing components. Such a sensor may be configured to convert thermal energy into electrical energy, and may comprise two or more thermocouples connected in series or in parallel. Such components may be configured to generate an output voltage proportional to a local temperature difference and/or temperature gradient. In an exemplary embodiment in which the one or more of the sensors 32, 34 comprises a thermopile, the temperature probe 10 may comprise, for example, an infrared temperature probe and/or other like infrared thermometer.

In an exemplary embodiment, the thermopile described above may be configured to assist in sensing a temperature of one or more additional objects positioned on and/or proximate the temperature probe 10. For example, such thermopiles may be configured to sense a temperature of the probe cover 30 upon insertion of the infrared temperature probe 10 into the probe cover 30. For example, in an embodiment in which the first sensor 32 comprises a thermistor and/or a thermocouple, and the second sensor 34 comprises a thermopile, the first sensor 32 may be configured to sense a temperature of the body cavity of the patient, and the second sensor 34 may be configured to sense a temperature of at least a portion of the probe cover 30.

To assist the thermopile in sensing a temperature of the probe cover 30, at least a portion of the probe cover 30 may be roughened, etched, scribed, knurled, coated, and/or otherwise modified. Such a modified portion 44 of the probe cover 30 may assist in reducing an infrared radiation of the probe cover 30. For example, the modified portion 44 may be characterized by an infrared radiation transmissivity that is less than an infrared radiation transmissivity of a remainder of the probe cover 30. Thus, the modified portion 44 of the probe cover 30 may substantially block infrared radiation that impinges thereon.

In exemplary embodiments in which at least one of the sensors 32, 34 comprises a thermopile, such a sensor may collect infrared radiation from the modified portion 44 once the probe cover 30 is disposed on the shaft 18. Such radiation may be emitted by the modified portion 44 and may, thus, be measured by the thermopile. Upon receiving such returned (reflected) radiation from the modified portion 44, the thermopile may utilize the return radiation to assist in measuring a temperature of the probe cover 30 and/or the modified portion 44. In such an exemplary embodiment, the thermopile of the second sensor 34 may be utilized to sense a temperature of the probe cover 30 while the thermocouple and/or thermistor of the first sensor 32 may be utilized to sense a temperature of the body cavity of the patient. As will be described in greater detail below, the sensors 32, 34 may be operably, controllably, electrically, and/or otherwise connected to a controller 52. In such an exemplary embodiment, the controller 52 may be configured to assist in calculating a predicted patient temperature based on the temperatures sensed by the first and second sensors 32, 34.

In a further embodiment, an exemplary infrared temperature probe 10 may utilize at least a portion of the thermal radiation emitted by the patient and/or the body cavity of the patient into which the temperature probe 10 has been inserted in order to estimate, infer, calculate, and/or otherwise determine a predicted patient temperature. Such an exemplary temperature probe 10 may utilize signals received by at least one of the first and second sensors 32, 34 to determine an amount of infrared radiation emitted by the patient. Using a known transmissivity and/or other characteristic of the patient, such infrared temperature probes 10 may be capable of determining a predicted patient temperature.

At least one of the sensors 32, 34 may additionally include at least one window, lens, and/or other like optical component 36 positioned proximate thereto. For example, such an optical component 36 may be disposed substantially flush and/or coplanar with the outer surface of the shaft 18. In an exemplary embodiment in which the shaft 18 is substantially cylindrical, such an optical component 36 may be substantially curved so as to match the radius of curvature of the shaft 18. Such optical components 36 may assist in, for example, focusing and/or transmitting infrared radiation between the thermopile and the body cavity of the patient. Such optical components 36 may also assist in protecting the thermopile, thermocouple, thermister, and/or other sensor components during use of the temperature probe 10, and may assist in forming a substantially fluid tight compartment within the shaft 18 so as to protect sensor components from contact with bodily fluids, cleaning solutions, and/or other liquids. It is understood that such optical components 36 may be substantially transparent to assist in the transmission of infrared radiation.

One or more of the operator interfaces 22 may also be operably connected to a heater 38 disposed proximate the distal end 12 of the temperature probe 10. Such a heater 38 may be, for example, a resistance heater and/or any other like heating component utilized in medical device applications. Such a heater 38 may be configured to assist in increasing a temperature of at least a portion of the shaft 18. For example, the heater 38 may be disposed within approximately 1 inch of the tip 16, and may be configured to provide localized heating of the tip 16 and/or a portion of the distal end 12. The heater 38 may be configured to increase the temperature of a portion of the shaft 18 to any known and/or desired temperature. In exemplary embodiments, the heater 38 may be configured to increase a portion of the probe 10 to a known temperature between approximately 90° F. and approximately 100° F. In further exemplary embodiments, the heater 38 may be configured to increase the temperature of a portion of the probe 10 to a known temperature between approximately 92° F. and approximately 93° F. Although FIG. 1 illustrates the heater 38 being disposed at the distal end 12 opposite the first temperature sensor 32, it is understood that, in additional exemplary embodiments, the heater 38 may be disposed distal to or proximal to the first sensor 32. In further exemplary embodiments, the second sensor 34 may be desirably spaced from the heater 38 so as not to be affected by heat generated by the heater 38. In exemplary embodiments, the second sensor 34 may be disposed and/or spaced proximal to the heater 38, and such spacing may be desirably selected so as to substantially thermally insulate the second sensor 34 from the heater 38. As described above with respect to the sensors 32, 34, the heater 38 may also be controllably and/or otherwise operatively connected to the controller 52 or one of the operator interfaces 22. The heater 38 may be embedded within and/or otherwise disposed beneath the outer surface of the shaft 18 so as to avoid direct contact between, for example, the heater 38 and the probe cover 30 during use. The heater 38 may be desirably positioned at any depth and/or other location within the shaft 18 to assist in facilitating a desirable heat dissipation pattern at the distal end 12 of the temperature probe 10. Such positioning of the heater 38 may assist in heating the distal end 12 to the desired temperature discussed above.

The handle 20 may also include one or more displays 54 operably connected to the controller 52. The display 54 may comprise, for example, a liquid crystal display (LCD) screen, a light emitting diode (LED) display, a digital read-out, and/or any other like components configured to communicate information to the user of the temperature probe 10. Such displays 54 may be configured to indicate, for example, one or more temperatures sensed by the sensors 32, 34, a temperature of the heater 38, one or more temperatures calculated based on signals received from the one or more sensors 32, 34, and/or any other information that may be useful during operation of the temperature probe 10. The display 54 may be configured to communicate such information substantially instantaneously and/or substantially continuously depending on the mode of operation of the temperature probe 10. Such a display 54 may also indicate whether or not the temperature probe 10 and/or the heater 38 is turned on, and whether a probe cover 30 has been connected to the temperature probe 10. The display 54 may also be configured to indicate the mode of operation of the temperature probe 10 (for example, continuous or instantaneous modes of temperature calculation), as well as whether one or more threshold temperatures, threshold temperature change rates, and/or other sensed metric thresholds have been met or exceeded. The display 54 may be, for example, a substantially numerical digital display, and may also be configured to display any other typical operating information such as, for example a temperature vs. time trend line or other graphical depictions.

The temperature probe 10 may also include one or more signal devices (not shown) operably connected to the controller 52. Such signal devices may include, for example, one or more lights, LEDs, speakers, and/or other like devices configured to emit an audible and/or optical or signal in response to a command or signal from the controller 52. Such an alarm or other signal may be initiated by, for example, the controller 52 when the calculated temperature meets or exceeds a threshold temperature. In additional exemplary embodiments, such an alarm or signal may be initiated during a substantially continuous temperature calculation operation where the rate of patient temperature change meets or exceeds a predetermined temperature change rate threshold. In additional exemplary embodiments, such signal/devices may be disposed on and/or otherwise associated with the controller 52.

The controller 52 may be operably connected to the operator interfaces 22, display 54, sensors 32, 34, heater 38, and/or other components of the temperature probe 10, and the controller 52 may be configured to control the operation of such components. In an exemplary embodiment, the controller 52 may be configured to receive signals, information, measurements, and/or other data from the first and second sensors 32, 34 of the temperature probe 10, and to calculate a predicted patient temperature based on the information received. The controller 52 may also be configured to execute one or more commands and/or control programs. For example, the controller 52 may be programmed to initiate one or more alarms in response to calculating a patient temperature that is greater than or equal to a predetermined threshold temperature. In an exemplary embodiment, such a threshold temperature may be approximately 100° F. In addition, the controller 52 may be configured to initiate such an alarm during a substantially continuous temperature calculation operation if the calculated temperature increases and/or decreases at a rate that is greater than or equal to a predetermined threshold temperature change rate. The controller 52 may comprise a processor, memory, and/or other known controller components to facilitate the functionality described herein.

In an exemplary embodiment, the controller 52 may be disposed within, for example, the handle 20 of the temperature probe 10. In such an embodiment, the controller 52 may be formed substantially integral with the temperature probe 10. For example, the handle 20 may form one or more substantially water-tight and/or substantially hermetically sealed compartments for storing the various components of the controller 52. Alternatively, as shown in FIG. 1, the controller 52 may be formed separately from the temperature probe 10. In such exemplary embodiments, the controller 52 may comprise a housing that is formed separate from the handle 20. To facilitate communication between the temperature probe 10 and the controller 52 in such embodiments, the controller 52 may be operably connected to the temperature probe 10 via one or more wires, cables, Bluetooth, WiFi, radio, and/or other known hard-wired and/or wireless communication protocols. The controller 52 and/or the temperature probe 10 may further include any number of ports, connectors, transponders, receivers, antennae, and/or other known components to facilitate such connectivity and/or communication. As shown in FIG. 1, in an exemplary embodiment in which the controller 52 is formed separate from the temperature probe 10, the controller 52 may comprise a display 54 and one or more operator interfaces 56. The display 54 and operator interfaces 56 of the controller 52 may be structurally and/or functionally similar to the display 54 and operator interfaces 22 of the handle 20 described herein.

The probe cover 30 may be substantially cylindrical, and may have similar dimensions to that of the shaft 18. For example, the probe cover 30 may be incrementally longer than the shaft 18 so as to fit over substantially the entire shaft 18. The probe cover 30 may define an orifice 46 at a proximal end 42 thereof. Similar to the shaft 18, the probe cover 30 may also define a substantially atraumatic tip at a distal end 40 thereof. The probe cover 30 may be formed from any medically approved material known in the art. Such materials may include, for example, plastics, polymers, and/or any of the other materials discussed above with regard to the temperature probe 10. Using such materials may enable, for example, the probe cover 30 to be repeatedly used and/or sanitized. Alternatively, in additional exemplary embodiments, the probe cover 30 may be configured for one-time usage. Such materials may also facilitate one or more known modifications to at least a portion of the probe cover 30. For example, such materials may facilitate defining the one or more modified portions 44 described above.

The modified portion 44 may be shaped, sized, located, and/or otherwise configured for interaction with one or more of the sensors 32, 34 of the temperature probe 10. For example, the modified portion may extend around substantially an entire circumference of the probe cover 30. The modified portion may have a length that is at least as long as the lens, or other optical component 36 covering the second sensor 34.

In additional exemplary embodiments, the probe cover 30 may include one or more additional structures to facilitate usage with, insertion on, and/or removal from the temperature probe 10. For example, while the orifice 46 may be shaped, sized, and/or otherwise configured to accept the shaft 18 and to mate with one or more ejector mechanisms 26 of the temperature probe 10, in further exemplary embodiments, at least a portion of the proximal end 42 of the probe cover 30 may include additional notches, cutouts, tabs, ribs, flanges, and/or other retention components configured to assist in connecting the probe cover 30 to and/or disconnecting the probe cover 30 from the temperature probe 10. For example, such retention components may mate with the ejector mechanisms 26 of the temperature probe 10 to facilitate retention of the probe cover 30 on the shaft 18 and/or ejection of the probe cover 30 from the shaft 18.

Figure 2:
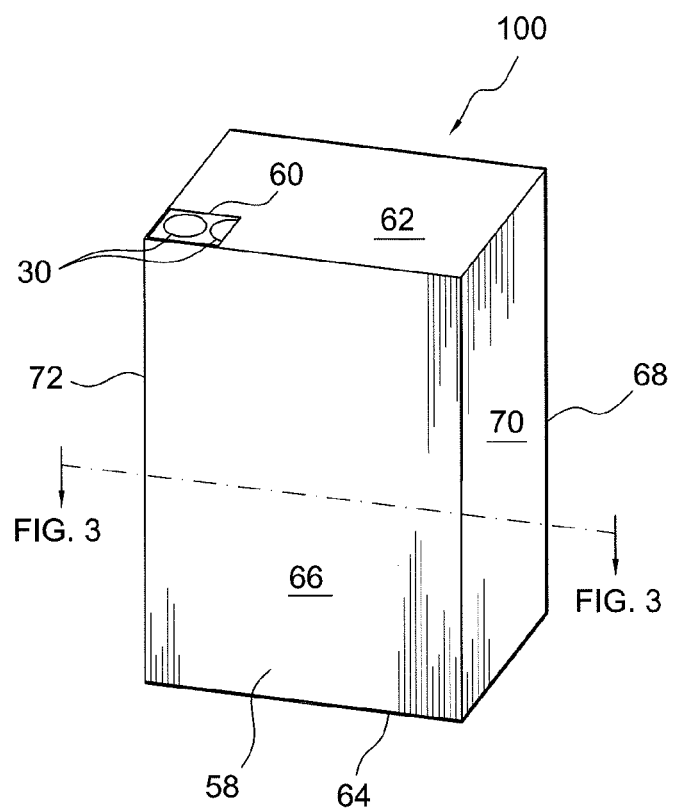
FIG. 2 illustrates a portion of a temperature measurement system according to an exemplary embodiment of the present disclosure.

As shown in FIG. 2, an exemplary temperature measurement system 100 of the present disclosure may include a storage container 58 and one or more probe covers 30 disposed within the storage container 58. Such an exemplary temperature measurement system 100 may also include the temperature probe 10 (FIG. 1) and any of its components. The storage container 58 may have any shape, size, and/or other configuration convenient for storing a plurality of probe covers 30 therein. For example, the storage container 58 may be substantially box shaped, and may have a substantially rectangular, substantially square, and/or substantially hexagonal cross-sectional shape. Such an exemplary cross-section of the storage container 58 is illustrated in FIG. 3.

At least a portion of the storage container 58 may define one or more openings 60. Such exemplary openings 60 may be shaped, sized, located, and/or otherwise configured to assist in the removal of one or more probe covers 30 from the storage container 58. For example, such an opening 60 may be shaped and/or sized to permit passage of a probe cover 30 for removal from the storage container 58. Such an opening 60 may also be shaped and/or sized to permit removal of only a single probe cover 30 from the storage container 58 at one time. In such an exemplary embodiment, the opening 60 may assist in retaining the remaining probe covers 30 within the storage container 58 while, at the same time, facilitating removal of a single probe cover 30 for use with the temperature probe 10.

As shown in FIG. 2, the storage container 58 may, for example, define a front 66, a back 68, and at least two sides 70, 72. In additional exemplary embodiments, it is understood that the storage container 58 may include additional sides and/or other structures depending upon, for example, the configuration of the probe covers 30 and/or storage requirements related to the probe covers 30. As shown in FIG. 2, an exemplary storage container 58 may also include a top 62, and a bottom 64 disposed opposite the top 62. In an exemplary embodiment, the top 62 may define at least a portion of the opening 60. In additional exemplary embodiments, at least a portion of the top 62 may be removed to expose the opening 60, and in further exemplary embodiments, substantially the entire top 62 may be removed from the storage container 58. In such exemplary embodiments, substantially all of the probe covers 30 disposed within the storage container 58 may be exposed for removal.

Figure 3:
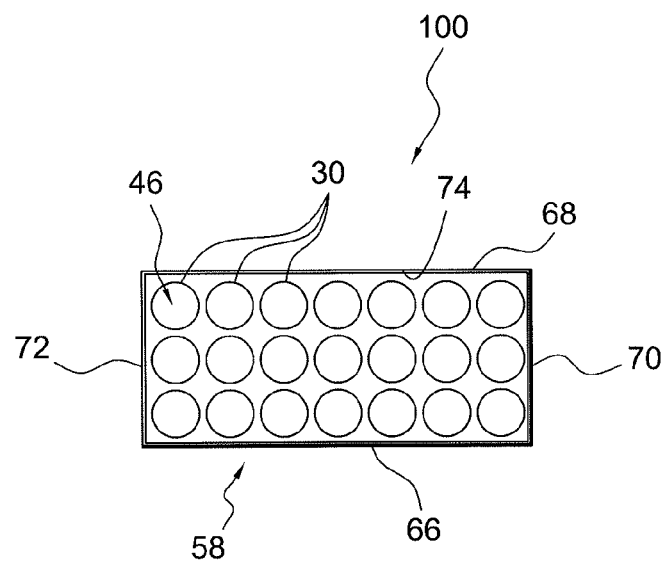
FIG. 3 is a cut away pictorial view of the portion of the temperature measurement system shown in FIG. 2.

As illustrated in FIG. 3, two or more probe covers 30 may be positioned adjacently within the storage container 58. For example, two or more such probe covers 30 may be substantially aligned along respective lengths thereof within the storage container 58. In such exemplary embodiments, a plurality of probe covers 30 may be supported by, for example, by the bottom 64 of the storage container 58 and may be arranged to stand within the storage container 58 on the respective distal ends 40 thereof. In an exemplary embodiment in which the storage container 58 is tipped and/or otherwise arranged to lay on the front 66, back 68, or sides 70, 72 thereof, the plurality of probe covers 30 may be substantially stacked on top of one another and/or otherwise positioned within the storage container 58. An example of such stacked alignment and/or adjacent positioning of the probe covers 30 is illustrated in FIG. 3.

The temperature probes 10, probe covers 30, and storage containers 58 described herein may be utilized by physicians, nurses, and/or other health care professionals in a variety of different environments. For example, the devices and/or the temperature measurement systems described herein may be employed in any of a number of examination facilities to determine one or more temperatures associated with a patient such as, for example, a predicted patient temperature. Such a predicted patient temperature may be utilized by the health care professional to assist in treating the patient, and may have a variety of uses that are well known in the medical field.

In order to determine a predicted patient temperature according to an exemplary embodiment of the present disclosure, a user of the temperature probe 10 may insert the temperature probe 10 into a probe cover 30. For example, the user may insert at least a portion of the temperature probe 30 such as, for example, the shaft 18 into the probe cover 30, via the orifice 46. In an exemplary embodiment, the probe cover 30 may be disposed within a storage container 58 while the shaft 18 of the temperature probe 10 is inserted into the probe cover 30. In such an exemplary embodiment, the probe cover 30 may be accessed through the opening 60 of the storage container 58 for insertion of the shaft 18. In such an exemplary embodiment, the temperature probe 10 may be moved in the direction of arrow 50 relative to the probe cover 30 for insertion. Alternatively, in exemplary embodiments in which the probe cover 30 has been removed from the storage container 58 before connection with the temperature probe 10, the probe cover 30 may be moved in the direction of arrow 48 relative to the temperature probe 10 to facilitate a connection with the temperature probe 10.

As one or more of the ejector mechanisms 26 come into contact with the probe cover 30, one or more such ejector mechanisms 26 may hook, clip, and/or otherwise mate with the proximal end 42 of the probe cover 30 to assist in retaining the probe cover 30 on the shaft 18. In exemplary embodiments in which the proximal end 42 of the probe cover 30 defines one or more of the notches, cutouts, and/or other retention components described above configured to mate with such ejector mechanisms 26, these components may communicate with the corresponding ejector mechanisms 26 of the temperature probe 10 to assist in retaining the probe cover 30 thereon.

Once the probe cover 30 has been connected to the temperature probe 10, one or more of the sensors 32, 34 may be activated and/or otherwise controlled to sense a first temperature. Such a temperature may be indicative of for example, a temperature of the probe cover 30. In an exemplary embodiment, sensing this first temperature with the temperature probe 10 may include sensing a temperature of the modified portion 44 of the probe cover 30. For example, once the temperature probe 10 has been inserted into the probe cover 30, one or more of the sensors 32, 34 may be disclosed in close proximity to the modified portion 44. For example, the modified portion 44 may be located and/or otherwise disposed at any desirable location along the outer and/or inner surface of the probe cover 30. Such a location may substantially coincide with a location of at least one of the sensors 32, 34 disposed on the shaft 18. In this way, the modified portion 44 may substantially overlay at least one of the sensors 32, 34 when the probe cover 30 is connected to the temperature probe 10. In an exemplary embodiment in which, for example, the second sensor 34 is positioned and/or otherwise configured to sense the first temperature described above, the modified portion 44 may substantially overlay the second sensor 34 when the probe cover 30 is connected to the temperature probe 10. In such an exemplary embodiment, the second sensor 34 may sense the temperature of the modified portion 44. In such an exemplary embodiment, the second sensor 34 may comprise at least one thermopile, and the modified portion 44 may be characterized by an infrared radiation transmissivity that is less than, for example, an infrared radiation transmissivity of the remainder of the probe cover 30. Such a difference in transmissivity may assist the second sensor 34 in sensing the temperature of the modified portion 44.

Once the temperature probe 10 has been inserted into the probe cover 30, the temperature probe 10 and the probe cover 30 may be inserted into a body cavity of a patient to facilitate determining a predicted temperature of the patient. For example, while within the body cavity, one or more of the sensors 32, 34 may sense a second temperature, and the second temperature may be indicative of a temperature of the body cavity. For example, in an embodiment in which the first sensor 32 comprises a thermocouple and/or a thermistor, the first sensor 32 may be utilized to measure the temperature of the body cavity.

Signals indicative of the measured first and second temperatures may be sent to the controller 52 by the first and second sensors 32, 34, and the controller 52 may assist in calculating the predicted patient temperature based on the first and second sensed temperatures. For example, knowing the temperature of the probe cover 30 may assist in accurately determining such a predicted patient temperature. In exemplary embodiments in which the probe cover 30 has a temperature that is either above or below the ambient temperature of the examination room and/or other location in which the temperature probe 10 is being utilized, the sensed temperature of the probe cover 30 may be utilized in the predicted patient temperature calculation to reduce error. Such error is commonly caused by mistakenly assuming that the probe cover 30 has a temperature substantially equal to such an ambient temperature when, in fact, the temperature of the probe cover 30 may be substantially different than the ambient temperature. Such differences in temperature may result from, for example, storing the probe cover 30 at a temperature below ambient.

Additional exemplary embodiments of the present disclosure may employ further techniques to assist in reducing the error associated with calculating the predicted patient temperature. For example, one such method of predicted patient temperature determination may include heating at least a portion of the temperature probe 10 to a known temperature, and calculating the predicted patient temperature based on the first and second sensed temperatures described above, as well as the known temperature. As described above with regard to the heater 38, the known temperature to which a portion of the temperature probe 10 may be heated may be between approximately 90° F. and approximately 100° F. For example, the known temperature may be between approximately 92° F. and approximately 93° F., and/or within any other useful temperature range. It is understood that the heater 38 may be utilized to assist in heating the portion of the temperature probe 10 to this known temperature.

In such exemplary embodiments, the heated portion of the temperature probe 38 may be located proximate the heater 38, and the heater 38 and the corresponding portion of the temperature probe 10 to be heated may be located within, approximately, 1 inch of the tip 16 of the temperature probe 10. It is understood that the controller 52 or one of the operator interfaces 22 may operate and/or otherwise control the heater 38 to heat the portion of the temperature probe 10 to such a known temperature, and this known temperature may provide a further metric and/or data point upon which the predicted patient temperature calculation may be based. Heating at least a portion of the temperature probe 10 in this way may bring the heated portion of the temperature probe 10 proximate the first sensor 32 to a temperature that is relatively close to the actual core temperature of the patient. Thus, the temperature of the body cavity measured by the second sensor 34 may be sensed more quickly since the time before the first sensor 32 reaches an equilibrium with the body cavity may be reduced. Additionally, accuracy of the predicted patient temperature calculation may be improved by heating the portion of the temperature probe 10 in this way since one or more algorithms utilized to, for example, extrapolate between the temperature sensed by the first sensor 32 and the actual temperature of the body cavity may have a higher precision when the first sensor 32 is at a temperature closely approximating the temperature of the body cavity. It is also understood that the first temperature indicative of the temperature of the probe cover 30 may be sensed either before the portion of the probe 10 is heated to the known temperature, such as upon insertion of the temperature probe 10 into the probe cover 30. Alternatively, the first temperature may be sensed while the portion of the temperature probe 10 is being heated to the known temperature discussed above.

In still further exemplary embodiments, one or more additional sensors 28 may be disposed on the temperature probe 10 at a location useful for detecting the presence of the probe cover 30. For example, such sensors 28 may be disposed proximate the base 24 of the shaft 18 and configured to detect the proximal end 42 of the probe cover 30 once the shaft 18 has been inserted into the probe cover 30. In still further exemplary embodiments, such sensors 28 may be disposed proximate the tip 16 and configured to detect the distal end 40 of the probe cover 30 once the shaft 18 has been inserted into the probe cover 30. In such exemplary embodiments, the one or more sensors 28 may comprise, for example, a proximity sensor and/or any other like sensing device, and sensing the first temperature indicative of a temperature of the probe cover 30 may be performed in response to detecting the presence of the probe cover 30 on the shaft 18.

It is understood that in any of the exemplary embodiments described herein, sensing the temperature indicative of the temperature of the probe cover 30 may be facilitated by activating one or more infrared temperature sensors of the temperature probe 10, such as one or more of the thermopiles described herein. In exemplary embodiments of calculating the predicted patient temperature, such a calculation may involve calculating a difference between the first and second sensed temperatures described above, and such a calculation may further include calculating a difference between the second temperature and the known temperature to which the portion of the temperature probe 10 has been heated.

Although the exemplary embodiments described above may utilize a first temperature indicative of a temperature of the probe cover 30 in determining the predicted patient temperature, in further exemplary embodiments, the predicted patient temperature may be determined utilizing a sensed first temperature indicative of a temperature of the storage container 58. In such an exemplary embodiment, a portion of the storage container 58 may be modified so as to reduce the infrared transmissivity of the modified portion of the storage container 58 relative to a remainder of the storage container 58. For example, at least a portion of an inner surface 74 (FIG. 3) of the storage container 58 may be modified utilizing any of the methods described above with regard to the modified portion 44 of the probe cover 30. The inner surface 74 may be roughened and/or coated to assist in at least partially reflecting infrared radiation. In an exemplary embodiment, a substantially black dye, paint, coating, and/or any other coating useful in at least partially reflecting infrared radiation may be disposed on one or more such inner surfaces 74 of the storage container 58. In such exemplary embodiments, one or more thermopiles of, for example, the second sensor 34 may be utilized to sense the temperature of the storage container 58 upon insertion of the temperature probe 10 into the probe cover 30, and while the probe cover 30 is disposed within the storage container 58. In such an exemplary embodiment, the modified portion 44 of the probe cover 30 may be omitted.

Forming the modified portion on one or more inner surfaces 74 of the storage container 58 may assist in reducing the cost of producing the temperature measurement system 100 described herein. For example, it may be less expensive to form such a modified portion on one or more inner surfaces 74 of the storage container 58 during manufacture of the storage container 58 than forming the modified portions 44 on each of the probe covers 30 individually utilized with the temperature probe 10. Thus, in an exemplary embodiment of determining a predicted patient temperature, the first temperature sensed with, for example, the second sensor 34 may be indicative of a temperature of the storage container 58. Such an exemplary method may further include one or more of the exemplary steps described above such as, for example, sensing a second temperature with the temperature probe 10 indicative of a temperature of the body cavity, and calculating the predicted patient temperature based on the first and second temperatures.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A system, comprising:
   a shaft having a central longitudinal axis, a distal end, a proximal end, and a substantially atraumatic tip disposed at the distal end of the shaft, the shaft defining a distal end of a temperature probe;
   a handle disposed at the proximal end of the shaft and defining a proximal end of the probe;
   a thermopile embedded substantially within the shaft and configured to measure a temperature of a probe cover removably connectable to the shaft by receiving radiation passing from the probe cover to the thermopile in a direction substantially transverse to the longitudinal axis;
   a temperature sensor disposed distal to the thermopile and embedded substantially within the shaft, the temperature sensor comprising at least one of a thermocouple or a thermistor configured to measure a body cavity temperature of a patient; and
   a controller operably connected to the thermopile and the temperature sensor, the controller being configured to determine a core temperature of the patient based at least partly on a first input received from the thermopile indicative of the temperature of the probe cover, and a second input received from the temperature sensor indicative of the body cavity temperature.

2. The system of claim 1, wherein at the shaft comprises at least one waterproof seal prohibiting fluids from contacting at least one of the thermopile or the temperature sensor.

3. The system of claim 1, wherein the handle includes an operator interface operably connected to the controller and configured to receive an input from a user of the system.

4. The system of claim 1, further comprising a heater configured to heat the distal end of the shaft to a known temperature, wherein the thermopile is spaced proximal to the heater such that the thermopile is substantially thermally insulated from the heater.

5. The system of claim 4, wherein the heater is disposed proximate the tip and the temperature sensor, and is embedded substantially within the shaft.

6. The system of claim 1, wherein the shaft includes a substantially fluid-tight compartment and a substantially transparent optical component forming at least part of the compartment.

7. The system of claim 6, wherein at least one of the thermopile or the temperature sensor is disposed substantially within the compartment, and wherein the optical component comprises at least one of a window, a lens, or a filter.

8. The system of claim 1, further comprising a display operably connected to the controller and disposed on the handle, the display comprising one of a liquid crystal display screen, a light emitting diode display, or a digital read-out, wherein the display is configured to display at least one of the temperature of the probe cover, the body cavity temperature, or the core temperature.

9. The system of claim 1, wherein the controller is disposed substantially within a housing separate from the handle.

10. The system of claim 1, wherein the temperature of the probe cover measured by the thermopile is different from an ambient temperature of an environment in which the system is being used.

11. The system of claim 1, wherein the direction is substantially transverse to a longitudinal axis of the shaft.

12. The system of claim 1, wherein the radiation passes to the thermopile at a location of the shaft proximal to the tip.

13. The system of claim 1, wherein the temperature sensor is disposed proximate the tip, and the thermopile is disposed proximal to the tip and is substantially thermally isolated from the tip.

14. A method of manufacturing a temperature measurement system, comprising:
providing a shaft having a central longitudinal axis, a distal end, a proximal end, and a substantially atraumatic tip disposed at the distal end of the shaft;
connecting the proximal end of the shaft to a distal end of a handle;
disposing a thermopile substantially within the shaft at a first location along the shaft, wherein the thermopile is configured to determine a temperature of a probe cover removably connectable to the shaft by receiving radiation passing from the probe cover to the thermopile in a direction substantially transverse to the longitudinal axis;
disposing a temperature sensor comprising at least one of a thermocouple or a thermistor substantially within the shaft at a second location along the shaft different from the first location, wherein the temperature sensor is configured to determine a body cavity temperature of a patient; and
operably connecting the thermopile and the temperature sensor to a controller configured to determine a patient temperature based on the temperature of the probe cover and the body cavity temperature.

15. The method of claim 14, further comprising forming a substantially water-tight compartment with at least a portion of the shaft, and disposing at least one of the thermopile or the temperature sensor substantially within the compartment, wherein at least part of the compartment is formed by a substantially transparent optical component positioned substantially flush with a substantially cylindrical outer surface of the shaft.

16. The method of claim 14, further comprising disposing a heater substantially within the shaft proximate the distal end of the shaft, and operably connecting the heater to the controller, wherein the heater is configured to selectively heat the distal end of the shaft to a known temperature.

17. The method of claim 14, further comprising operably connecting the controller to a display, wherein the display comprises a component of the handle.

18. The method of claim 14, further comprising:
providing a storage container configured to retain a plurality of probe covers, the storage container including an opening, at least two sides, and a bottom extending from the at least two sides; and
modifying a first portion of the storage container such that the first portion of the storage container is characterized by a first infrared radiation transmissivity and a second portion of the storage container is characterized by a second infrared radiation transmissivity greater than the first infrared radiation transmissivity.

19. The method of claim 14, further comprising modifying a first portion of the probe cover such that the first portion of the probe cover is characterized by a first infrared radiation transmissivity and a second portion of the probe cover is characterized by a second infrared radiation transmissivity greater than the first infrared radiation transmissivity.

20. The method of claim 19, wherein the first portion is disposed at a location on the probe cover substantially coinciding with the first location such that the first portion substantially overlays the thermopile when the probe cover is removably connected to the shaft.

21. A system for determining a patient temperature, comprising:
a probe cover removably connectable to a temperature probe, the probe cover having a first portion characterized by a first infrared radiation transmissivity and a second portion characterized by a second infrared radiation transmissivity greater than the first infrared radiation transmissivity, the probe cover including an orifice configured to receive a shaft of the temperature probe, the shaft having a central longitudinal axis, wherein the temperature probe further includes:
a handle disposed proximal to the shaft,
a thermopile embedded substantially within the shaft at a first location along the shaft, wherein the thermopile is configured to determine a temperature of the probe cover by receiving radiation passing from the probe cover to the thermopile in a direction substantially transverse to the longitudinal axis, and
a temperature sensor embedded substantially within the shaft at a second location along the shaft different from the first location, wherein the temperature sensor is configured to determine a body cavity temperature of a patient, the system being configured to determine the patient temperature based on the temperature of the probe cover and the body cavity temperature.

22. The system of claim 21, wherein the first portion of the probe cover is at least one of roughened or coated with a substantially infrared radiation reflective coating, and the temperature of the probe cover comprises a temperature of the first portion.

23. The system of claim 21, wherein the first portion is disposed at a location on the probe cover substantially coinciding with the first location such that the first portion substantially overlays the thermopile when the probe cover is removably connected to the shaft.

24. The system of claim 21, wherein the first portion is configured to substantially block infrared radiation impinging thereon.

25. The system of claim 21, wherein the probe cover is substantially cylindrical and first portion extends around substantially an entire circumference of the probe cover.

26. A system, comprising:
- a shaft having a distal end, a proximal end, and a substantially atraumatic tip disposed at the distal end of the shaft, the shaft defining a distal end of a temperature probe;
- a handle disposed at the proximal end of the shaft and defining a proximal end of the probe;
- a thermopile embedded substantially within the shaft and configured to measure a temperature of a probe cover removably connectable to the shaft, wherein the thermopile is disposed proximal to the tip such that the thermopile is substantially thermally isolated from the tip;
- a temperature sensor disposed distal to the thermopile and embedded substantially within the shaft at a location proximate the tip, the temperature sensor comprising at least one of a thermocouple or a thermistor configured to measure a body cavity temperature of a patient; and
- a controller operably connected to the thermopile and the temperature sensor, the controller being configured to determine a core temperature of the patient based at least partly on a first input received from the thermopile indicative of the temperature of the probe cover, and a second input received from the temperature sensor indicative of the body cavity temperature.

* * * * *